United States Patent [19]

Cannon

[11] 4,314,567
[45] Feb. 9, 1982

[54] DROP CONTROLLER

[75] Inventor: Raymond E. Cannon, San Diego, Calif.

[73] Assignee: IMED Corporation, San Diego, Calif.

[21] Appl. No.: 78,573

[22] Filed: Sep. 24, 1979

[51] Int. Cl.³ .............................................. A61M 5/00
[52] U.S. Cl. ............................ 128/214 F; 128/214 E; 128/214 C; 128/273; 128/DIG. 12; 128/DIG. 13
[58] Field of Search .......... 128/214 C, 214 E, 214 F, 128/274, DIG. 12, DIG. 13

[56] References Cited

U.S. PATENT DOCUMENTS 4,067,332  1/1978  O'Leary ........................ 128/273 X
4,126,132  11/1973  Portner et al. ................. 128/273 X Primary Examiner—Henry K. Artis
Attorney, Agent, or Firm—Ellsworth R. Roston; Charles H. Schwartz

[57] ABSTRACT

A drop controller is provided for controlling the rate at which drops of a fluid flow to a patient. The drop controller includes a socket for receiving a cassette having a constrainable member adjustable in position. This constrainable member controls the size of an adjustable passage through which the fluid flows to the patient. The socket is defined by a plurality of spring fingers for releasably holding the cassette. A lever is mounted on the housing for the drop controller and is pivotable to a cocked position by the cassette when the cassette is disposed in the socket. The lever can be pivoted to a second position to obtain a removal of the cassette from the socket.

34 Claims, 5 Drawing Figures

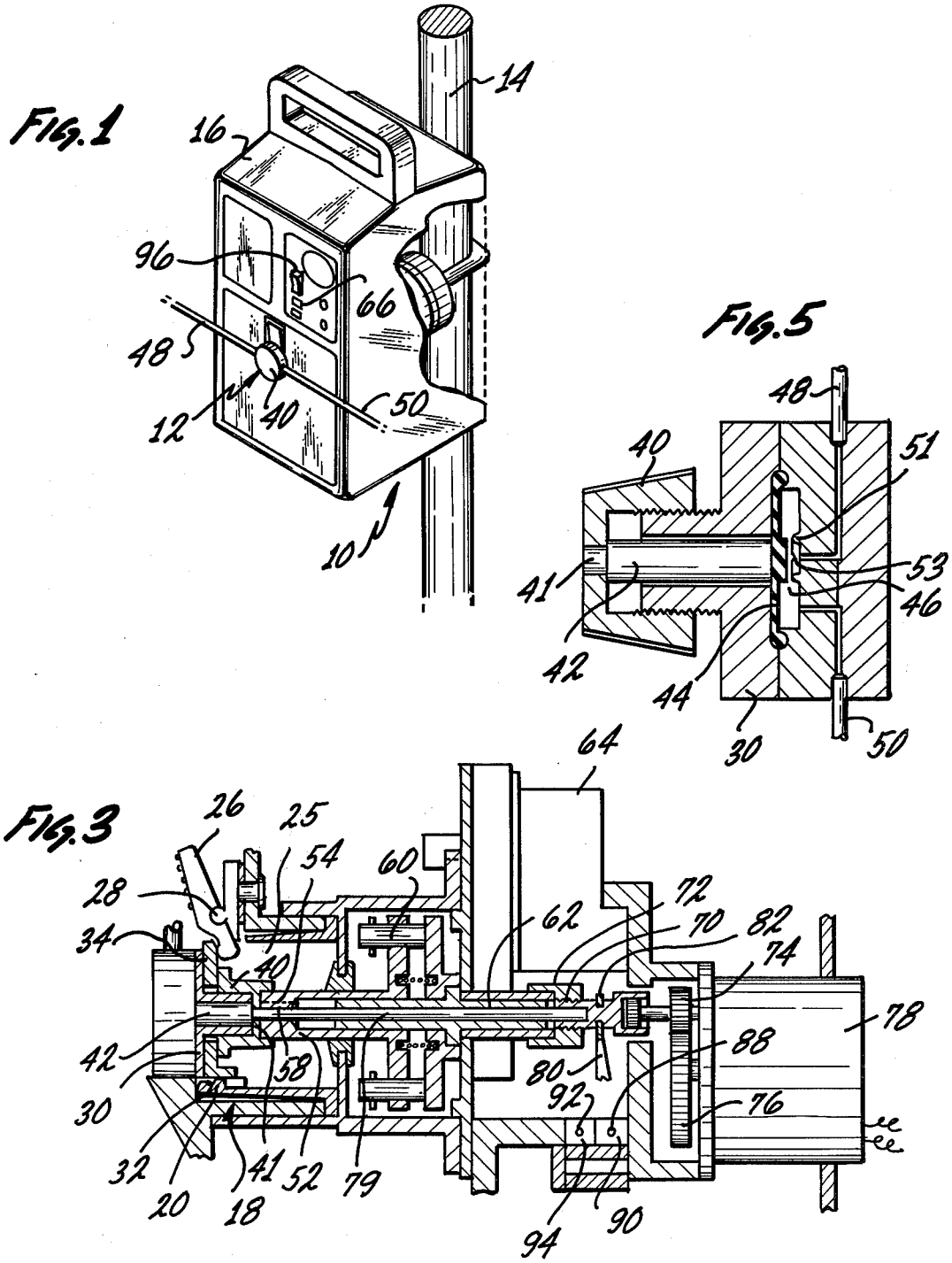

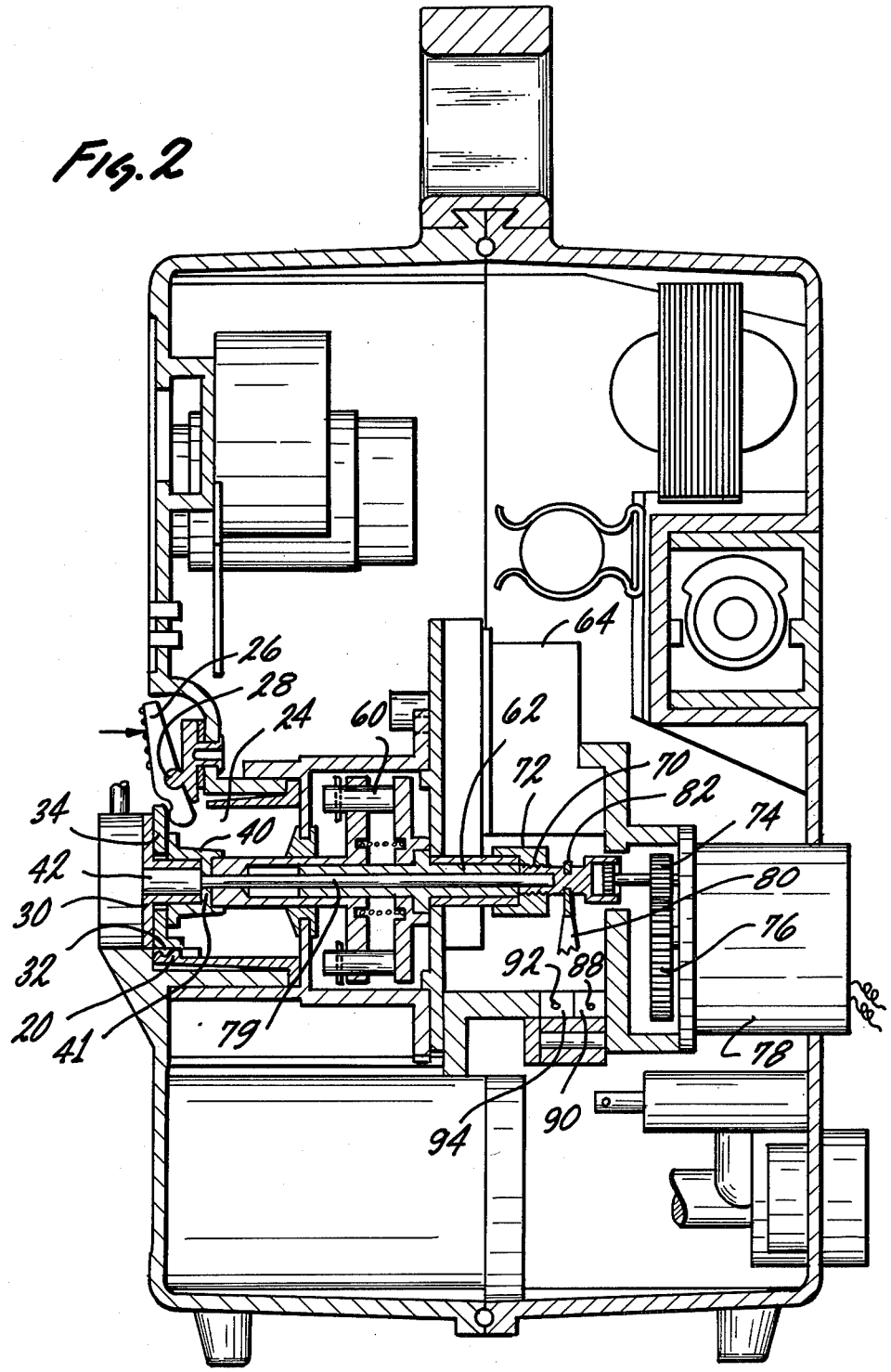

DROP CONTROLLER

This invention relates to a drop controller for controlling the rate at which drops of fluid flow to a patient. More particularly, the invention relates to a drop controller including a disposable cassette through which the fluid flows to the patient. The invention especially relates to a drop controller which provides for a fixed, but easily releasable, relationship between the controller and the cassette. The invention further relates to a controller having fail-safe features for insuring that fluid will flow through the cassette only at proper times and at pre-set rates.

As the practice of medicine becomes progressively complex and refined, the equipment and techniques used to provide care for a patient have become increasingly sensitive in order to assure that the patient receives optimum care. For example, after an operation has been performed on a patient and the patient is in the recuperative state, intravenous fluid has often been introduced to the patient. The rate of introduction of fluid to the patient is dependent upon a number of different factors including the weight, age, sex and physical state of the patient. As the patient recovers from his illness, the rate of introduction of the intravenous fluid to the patient is preferably adjusted to assure that the patient receives an optiumum benefit from the fluid.

Drop controllers have been used in the prior art to control the rates at which drops of fluid have flowed to a patient. Such drop controllers have been relatively crude. They have provided for the clamping of a conduit to control the rate at which fluid flows. Such clamping has been relatively unreliable in controlling the rate of fluid flow.

Copending application Ser. No. 938,910 has been filed by me on Sept. 1, 1978, for "Apparatus for Controlling the Flow of Intravenous Fluid to a Patient" now abandoned and has been assigned of record to the assignee of record of this application. This copending application discloses and claims a disposable cassette which passes fluid at a controlled rate to a patient. The cassette can be used by itself to provide an accurate control over the flow of fluid at a preselected rate in accordance with the manual operation of a knob included in the cassette. The cassette can also be disposed in a drop controller to provide for a precise flow of fluid through the cassette in accordance with the operation of settings provided on the face of the controller. The electronic settings have precedence over any manual positioning of the knob. In this way, the cassette can be controlled either manually or electronically.

Furthermore, each cassette can be discarded after use by a single patient and a new cassette can be provided for the next patient without any need to sterilize the drop controller between uses.

This invention provides an improved drop controller for use with the cassettes disclosed and claimed in application Ser. No. 938,910. The drop controller provides for a fixed, but easily releasable, coupling between the cassette and the controller. The drop controller also includes apparatus for controlling the size in the cassette of the passage providing for the flow of fluid and further includes apparatus for closing this passage when the control apparatus is not functioning properly. The invention further includes apparatus for testing the operation of the drop controller before every use of the controller by closing and then opening the passage. Apparatus is also included for providing for an adjustable disposition of the controller on a support pole.

The drop controller includes a socket for receiving a cassette having a constrainable member adjustable in position. This constrainable member controls the size of a passage through which the fluid flows to the patient. The socket is defined by a plurality of spring fingers for releasably holding the cassette. A lever is mounted on the housing for the controller and is pivotable to a first position by the cassette when the cassette is disposed in the socket. The lever can be pivoted manually to a second position to obtain a removal of the cassette from the socket.

Coupling means are disposed in the controller housing for controlling the positioning of the constrainable member in accordance with the activation of settings on the face of the housing. A stepper motor is operable to adjust the position of the constrainable member in accordance with the activation of the settings. A second motor is also disposed in the motor for driving the member. The second motor becomes operative to drive the member to the closed position of the passage if the stepper motor should become inoperative. The second motor also becomes operative to drive the first member initially to the closed position of the passage when the operation of the drop controller is initiated. After the constrainable member has been driven to the closed position, it is driven by the second motor to the open position. In this way, the second motor acts to test the proper operation of the drop controller.

An arrangement is also included for releasably and adjustably positioning the controller relative to a support pole. The arrangement incudes a shaft and an arm at the end of the shaft for providing an engagement of the support pole between the arm and the housing of the controller. The arrangement further includes a rotatable knob for pivoting the controller on the pole so that the front face of the controller can be easily viewed by hospital attendants.

In the drawings:

FIG. 1 is a perspective view, partially broken away, of a drop controller and a cassette in operatively coupled relationship and further illustrates the disposition of the controller on a support pole;

FIG. 2 is an enlarged elevational view, in section, of the controller and cassette shown in FIG. 1;

FIG. 3 is an elevational view, in section, similar to that shown in FIG. 2 but restricted to the cassette and that portion of the controller providing some of the important features of the invention;

FIG. 5 is a schematic view, partially in section, of the cassette shown in FIGS. 1, 2 and 3.

Figure 4:
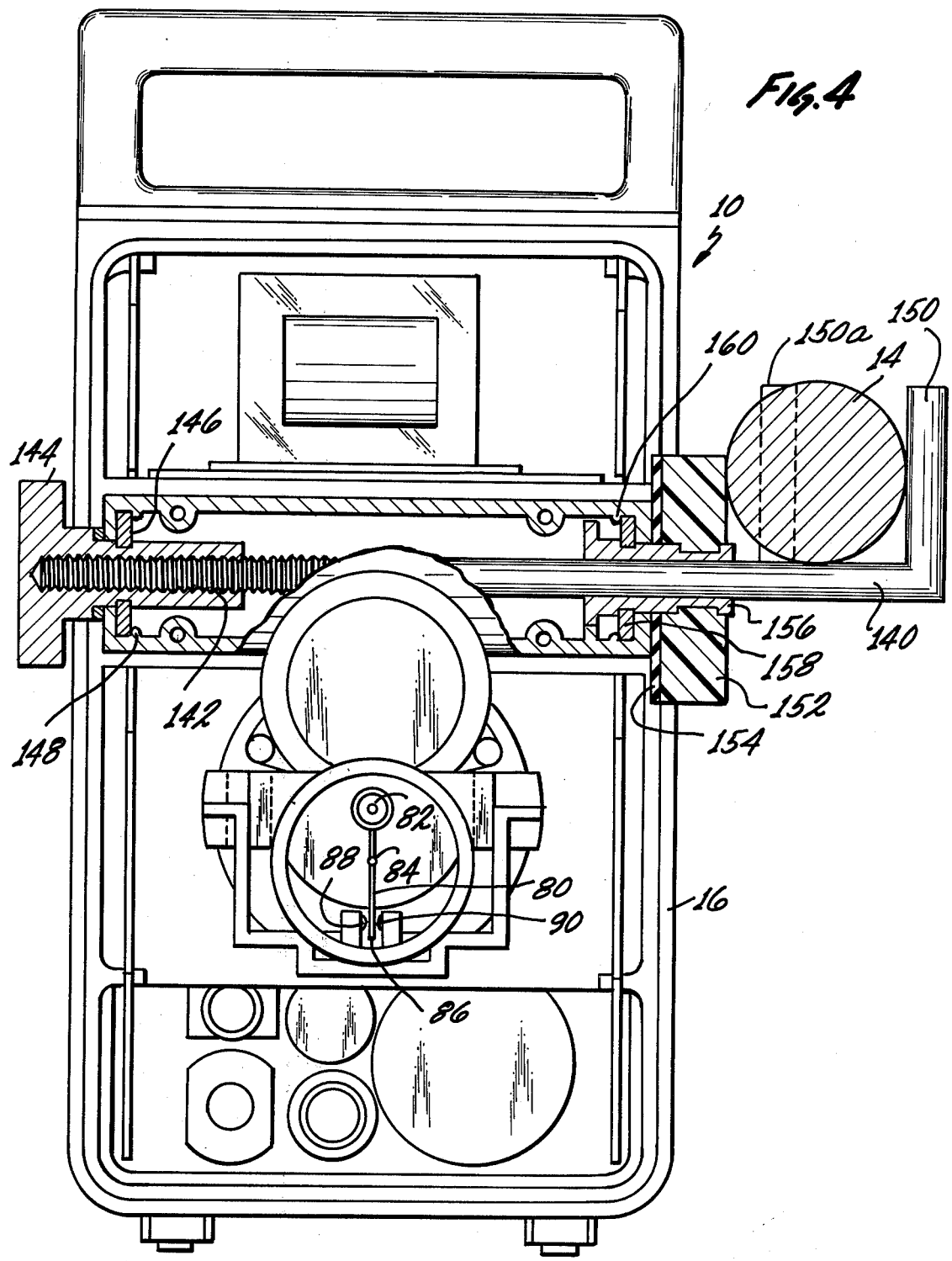
FIG. 4 is an enlarged plan view, in section, of the controller and of the arrangement for adjustably and releasably supporting the controller on a support pole.

In the embodiment of the inventions shown in the drawings, a drop controller generally indicated at 10 is provided. The drop controller may be adapted to operate in conjunction with a cassette, generally indicated at 12, to control the rate at which fluid, such as intravenous fluid, flows to a patient. The drop controller 10 and the cassette 12 may be constructed as described and shown in copending application Ser. No. 938,910. The drop controller is adapted to be supported on a pole 14.

The drop controller 10 includes a housing 16. The housing 16 includes a plurality of spring fingers 18 having detents 20 at or near their spring ends. The spring fingers are disposed in an annular configuration to define a socket 24. A lever 26 is pivotably supported at an intermediate position by a button 28 on the housing so as to define a relatively short lever arm below the button 28 and a relatively long lever arm above the button. The lower lever arm is disposed in the socket in one pivotable position, as shown in FIGS. 2 and 3.

The cassette 12 is provided with a housing 30 having detents 32 for cooperating with the detents 20 to retain the cassette in fixed position when the cassette is inserted into the socket. The cassette 12 is also provided with a wall 34 against which the lower arm of the lever 26 is disposed when the cassette is retained by the spring fingers 18 within the socket 24. When it is desired to remove the cassette 12 from the socket 24, the upper arm of the lever 26 is pressed toward the right in FIGS. 2 and 3. This produces a multiplication of force on the lower arm of the lever 26 to remove the cassette from the socket.

The cassette 12 may be provided with a rotatable knob 40 which is disposed within the controller housing 16 when the cassette is retained within the socket 24. The knob is open at a central position as indicated at 41. The knob 40 presses against a pusher rod 42 to control the positioning of a resilient diaphram 44 in a passage 46. The passage 46 communicates with an inlet conduit 48 and an outlet conduit 50. A button 51 is disposed in a closed loop at a position enveloping one of the inlet conduit 48 and the outlet conduit and a notch 53 is cut in the button. The notch 53 is closed by the diaphragm 44 through a distance dependent upon the rotational setting of the knob 40. In this way, the knob 40 acts on the pusher rod 42 to control the size of the opening defined by the passage, thereby controlling the rate at which drops of fluid flow through the passage 46.

A pusher member 52 is disposed in the controller 10 and is coupled to the knob 40 by a detent arrangement 54, preferably spring-biased, when the cassette 12 is properly positioned in the socket 24. The pusher member is in turn coupled through a yoke 60 to a hollow drive member 62 in a stepper motor 64. The motor 64 is stepped through a number of precise increments dependent upon the selection of digital settings 66 on the front of the housing 16. When the motor 64 is incrementally operated, it rotatably adjusts the positioning of the pusher member 52 and the member 52 in turn rotatably drives the knob 40 to constrain the diaphragm 44 and thereby adjust the size of the opening in the passage 46. The positioning of the pusher member 52 has precedence, in controlling the size of the opening in the passage 46, over any setting made manually in the knob 40 before the insertion of the cassette into the socket.

A threaded extension 70 is rotatably disposed within an internally threaded collar 72 having a stationary disposition. The threaded extension 70 is driven by a gear 74 which is in mesh with a gear 76 driven by a suitable motor 78 such as a D.C. motor. The threaded extension in turn drives a rod 79 which extends through the opening 41 in the knob 40 and presses against the pusher rod 42.

A yoke 80 is suitably mounted on the threaded extension 70 as by a sleeve 82. The yoke 80 is pivotably mounted as at 84 at an intermediate position along its length. The yoke 80 is provided at its outer length with a flag 86 which is movable at one extreme position between a light source 88 and a photocell 90 and at an opposite extreme position between a light source 92 and a photocell 94.

The photocells 90 and 94 and the motors 64 and 78 are included in electrical circuitry (not shown). The motor 78 is driven in opposite directions after the cassette 12 has been properly inserted into the controller 10 and when the operation of the controller is initiated by the closure of a switch 96 on the front of the housing 16 and the digital settings 66 have been set to a particular value. The operation of the motor 78 causes the rod 79 to be pressed against the pusher rod 42 and the diaphragm to be constrained in a direction for initially closing the passage 46 and for subsequently opening the passage. This insures that the passage 46 can be closed by the motor 78 if the controller 10 becomes inoperative in any way. In this way, a patient cannot be subjected to injury as a result of an improper operation or an inoperation of the controller 10.

FIG. 4 illustrates an arrangement for fixedly but releasably attaching the controller 10 to the support pole 14. The arrangement includes a shaft 140 threaded as at 142 at one end of the housing 16. A knob 144 is threadedly disposed on the threaded end of the shaft 140. The knob 144 is fixedly disposed relative to the housing as by a support clamp 146 and a button 148 for retaining the clamp in fixed positioning. The knob 144 extends outwardly from the housing to provide for a rotation of the knob and the housing relative to the shaft 140 in accordance with the manual operation of the knob.

The shaft 140 extends through the housing and emerges from the housing at the end opposite the knob 140. At this opposite end, the shaft 140 terminates in an arm 150 which extends in a direction substantially perpendicular to the shaft. The distance of the arm 150 from the end of the housing 16 can be adjusted by rotating the shaft relative to the knob 140, as may be seen by another positioning of the arm 150 in broken lines (designated as 150a). In this way, the arm 150 can be disposed against one side of the pole 14 and the housing 16 can be disposed against the other side of the pole to lock the drop controller in fixed position on the pole.

A block 152 may be disposed at the end of the housing 16 adjacent the pole 14 to cushion any force exerted on the housing by the pole. This cushioning effect is facilitated by a gasket 154 made from a suitable resilient material such as rubber. The block 152 and the gasket 154 may be fixedly positioned on a collar 156 which extends through the housing 16. The collar 156 is in turn fixedly positioned by a gasket 158 which is limited in axial movement by a button 160.

The housing 16 may be fixedly supported on the pole 14 by rotating the shaft 140 relative to the knob 144 to position the arm 150 against the pole. The knob 144 may then be rotated to tilt the housing 16 to any desired angle. This facilitates the viewing of the front face of the housing 16 by a short person disposed below the drop controller or by a tall person disposed above the drop controller.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination in a drop controller for use with a cassette having a detent to hold the cassette in fixed but removable relationship to the drop controller,
a housing, a plurality of detent means extending from the housing and having springlike characteristics for releasably holding the detent means on the cassette and having a looped configuration defining a socket for insertion of the cassette into the socket, pin means supported by the housing, and lever means mounted on the pin means and having a first arm and a second arm longer than the first arm and having first and second pivotable dispositions, the second arm being disposed for engagement by the cassette, upon the movement of the cassette into the socket, to become pivoted to the first position and being disposed in the first position in the housing in engagement with the cassette, the first arm being disposed externally of the housing for manual operation for removing the cassette from the socket.

2. The combination set forth in claim 1, wherein a knob extends from the cassette for manual adjustment and controls the size of an opening providing in the cassette for the flow of fluid and wherein a rod is disposed in the cassette and settings are provided on the housing for providing for a positioning of the rod to control the size of the opening.

3. The combination set forth in claim 1 wherein the cassette is provided with an adjustable passage and means including a rotatable knob are provided in the cassette for controlling the size of the passage and means are included in the controller and are associated with the rotatable knob for rotating the knob to control the size of the passage through the cassette.

4. The combination set forth in claim 1 wherein means are disposed in the housing for checking the opening and closing of the passage through the cassette before the initiation of each operation of the controller.

5. In combination for releasably retaining a disposable cassette in operative relationship to a drop controller and for providing for an adjustment in the flow of fluid through the cassette, a socket in the drop controller for releasably receiving the cassette, detent means on the cassette and the controller for releasably retaining the cassette in the socket, means adjustably disposed in the cassette and defining a passage having an opening variable in accordance with its adjustments in disposition, an external knob included in the cassette and manually rotatable to adjust the position of the passage means, and an arm pivotably supported on the controller and rotatable between first and second positions, the arm being rotatable to the first position in accordance with the insertion of the cassette into the socket and being manually rotatable to the second position, the arm being disposed in the first position to engage the cassette to provide for a removal of the cassette from the socket upon the pivotal movement of the arm to the second position.

6. The combination set forth in claim 5 wherein the drop controller includes a first motor for positioning the passage means and further includes means having adjustable settings for providing a controlled operation of the motor to adjust the opening in the passage in accordance with such setting.

7. The combination set forth in claim 6 wherein the drop controller includes a second motor for positioning the passage means and wherein means are included for obtaining an operation of the second motor upon an initiation in the operation of the controller and wherein means are included for operating the motor to move the passage means initially in a first direction for opening the passage and subsequently in a second direction for closing the passage.

8. The combination set forth in claim 7 wherein a pusher rod is positioned in the cassette against the adjustably disposed means and the knob is provided with an opening and a pusher member is disposed in the drop controller in coupled relationship with the knob and is movable to control the size of the passage and wherein the first motor is coupled to the shaft for driving the pusher member and wherein a shaft is extended through the opening in the knob into engagement with the pusher rod to position the pusher rod in accordance with the operation of the second motor.

9. In combination in a drop controller for use with a cassette having a member adjustable in position to control the size of a passage for the flow of drops of a fluid through the cassette, means included in the drop controller for providing an indication of the rate at which the drops are to flow through the cassette, first motor means in the drop controller for adjusting the positioning of the member in the cassette in accordance with the operation of the rate indicating means, second motor means in the drop controller for driving the member between the open and closed conditions of the passage, and means responsive to an initiation in the operation of the drop controller for energizing the second motor means to initially drive the member to a position for closing the passage and to subsequently drive the member to a position for opening the passage.

10. The combination set forth in claim 9 wherein a pusher member is provided in the drop controller and is coupled to the first motor means for operation by the first motor means to adjust the position of the adjustable member and a second member is provided in the drop controller and is coupled to the second motor means for operation by the second motor means to adjust the position of the adjustable member.

11. The combination set forth in claim 10 wherein means are operative by the second motor means to obtain the production of a first signal representing the closing of the passage and wherein means are operative by the second motor means to obtain the production of a second signal representing the opening of the passage.

12. The combination set forth in claim 9 wherein means are provided in the drop controller for holding the cassette in fixed but releasable relationship and wherein means are provided in the drop controller for obtaining a release of the cassette from the controller.

13. In combination in a drop controller for use with a cassette having a member adjustable in position to control the size of a passage for the flow of drops through the cassette, a housing, a socket in the housing for receiving the cassette, spring arms disposed in the socket for releasably holding the cassette, and a lever pivotably supported by the housing at an intermediate position to define first and second arms, the lever being disposed relative to the socket for movement of one of the arms by the cassette during the movement of the cassette into the socket and for release of the cassette from the socket upon the manual operation of the second arm of the cassette.

14. The combination set forth in claim 13 wherein a pusher member is disposed in the housing for disposition against the adjustable member to control the size of the passage and wherein means are provided in the housing for positioning the pusher member to control the size of the opening.

15. The combination set forth in claim 13 wherein means are provided on the housing for adjustable and releasable attachment of the drop controller to a support pole.

16. The combination set forth in claim 14 wherein means are disposed in the housing and are coupled to the adjustable member for closing the opening in the passage when the means for positioning the pusher member becomes inoperative.

17. The combination set forth in claim 16 wherein the passage-closing means includes a pusher rod disposed against the adjustable member and further includes a second motor energizable to drive the pusher rod in a direction for closing the passage when the means for positioning the pusher member becomes inoperative.

18. In combination for use with a drop controller to provide an adjustable positioning of the drop controller on a support pole, a housing, a shaft threaded at one end and extending through the housing, a rotatable knob extending from the housing at one end of the housing and threadedly disposed on the threaded end of the shaft, the knob being coupled to the housing in accordance with the rotation of the knob when the housing has been fixedly disposed on the support pole, an arm extending from the end of the shaft opposite the threaded end for engaging the pole between the housing and the arm, and means disposed on the housing at the end opposite the knob for cushioning the force of the pole on the housing.

19. The combination set forth in claim 18 wherein means are provided in the housing for retaining the knob in fixed relationship to the housing and means are disposed on the shaft for retaining the cushioning means at the end of the housing.

20. In combination in a drop controller for use with a cassette having a member adjustable in position to control the size of a passage for the flow of drops of a fluid through the passage and having a knob rotatable to adjust the position of the member, a first motor disposed relative to the knob for rotating the knob to adjust the position of the member, a second motor disposed relative to the member to adjust the position of the member, and means for releasably coupling the cassette to the drop controller in position to obtain a coupling between the first motor and the knob and between the second motor and the member.

21. The combination set forth in claim 20 wherein the knob is provided with an opening to expose the member in the cassette for direct coupling, including, first means operably coupled to the first motor and having a hollow configuration for coupling to the knob at peripheral positions on the knob for rotation of the knob in accordance with the operation of the first motor to adjust the position of the member, and second means operably coupled to the second motor and extending through the first means and the opening in the knob to adjust the position of the member in accordance with the operation of the second motor.

22. The combination set forth in claim 21, including, means cooperative with the second means for indicating the operation of the second means by the second motor to a position providing a closure of the passage, and means cooperative with the second means for indicating the operation of the second means by the second motor to a position providing an opening of the passage.

23. The combination set forth in claim 21 wherein the first motor constitutes a stepper motor and the second motor constitutes a continuously operable motor.

24. In combination in a drop controller for use with a cassette having a member adjustable in position to control the size of a passage for the flow of drops of a fluid through the passage and having a knob rotatable to adjust the position of the member, a first motor, a second motor, first means operably coupling the first motor to the knob for rotating the knob to adjust the position of the member, and second means operably coupling the second motor to the member for directly driving the member in accordance with the operation of the second motor.

25. The combination set forth in claim 24, including, the first means being disposed in enveloping relationship to the second means, a housing having a panel with an external face, and means disposed on the external face of the panel and operable to control the rotation of the knob by the first motor.

26. The combination set forth in claim 24 wherein the cassette has input and output lines communicating with the passage, including, a housing having a panel, and means for releasably retaining the cassette with the knob and the member disposed within the housing and with the input and output lines external to the housing panel.

27. The combination set forth in claim 26, including, the retaining means including a lever supported on the panel and extending externally of the panel and movable between the first and second positions and further including springlike fingers supported by the housing and having first and second positions and engageable by the lever in the first position of the lever for movement to the first position and operable in the first position to engage the cassette in fixed position relative to the housing and operable in the second position to release the cassette for removal from the housing and movable to the second position with the lever in the second position.

28. The combination set forth in claim 26, including, the lever being pivotable between the first and second positions and the fingers enveloping the cassette and being pivotable at one end and having detents at their other end for engaging the cassette in their first position.

29. The combination set forth in claim 24, including, the first motor being a stepper motor,
the second motor being a continuously operable motor,
means movable with the second means in a direction closing the passage for indicating the closure of the passage, and
means movable with the second means in a direction opening the passage for indicating the opening of the passage.

30. In combination in a drop controller for use with a cassette having a member adjustable in position to control the size of a passage for the flow of drops of a fluid through the passage and having a knot rotatable to adjust the position of the member,
a first motor operatively coupled to the knob for rotating the knob to adjust the member,
a second motor operatively coupled to the member for adjusting the member,
light source means,
flag means movable with the member, and
light sensor means disposed relative to the light source means for indicating the disposition of the member in the closed position of the passage and in the opened position of the passage.

31. The combination set forth in claim 30, including, the first motor constituting a stepper motor, and
the second motor constituting a continuously operable motor.

32. The combination set forth in claim 30, including, a housing,
the light source means being fixedly disposed in the housing, and
the light sensor means including a first light sensor fixedly disposed in the housing relative to the light source means and the flag means for producing a signal at the closed position of the passage and a second light sensor fixedly disposed in the housing relative to the light source means and the flag means for producing a signal at the opened position of the passage.

33. The combination set forth in claim 32, including, first means operatively coupling the first motor and the knob for rotating the knob, in accordance with the operation of the first motor, to move the member, and
second means operatively coupling the second motor and the member for driving the member in accordance with the operation of the second motor.

34. The combination set forth in claim 32, including, the first means enveloping the second means and the second means extending through a hole in the cassette to engage the member and the first motor constituting a stepper motor and the second motor constituting a continuously operable motor.

* * * * *